(12) United States Patent
Miltz et al.

(10) Patent No.: US 8,017,667 B2
(45) Date of Patent: Sep. 13, 2011

(54) ANTIMICROBIAL PACKAGING MATERIAL

(75) Inventors: Joseph Miltz, Haifa (IL); Stephen William Bigger, Vic (AU); Cornelis Sonneveld, Vic (AU); Pannuwat Suppakul, Bangkok (TH)

(73) Assignees: Victoria University, Footscray (AU); Technion Research and Development Foundation Ltd., Haifa (IL)

( * ) Notice: Subject to any disclaimer, the term of this patent is extended or adjusted under 35 U.S.C. 154(b) by 449 days.

(21) Appl. No.: 11/571,376

(22) PCT Filed: Jun. 27, 2005

(86) PCT No.: PCT/AU2005/000916
§ 371 (c)(1), (2), (4) Date: May 11, 2008

(87) PCT Pub. No.: WO2006/000032
PCT Pub. Date: Jan. 5, 2006

(65) Prior Publication Data
US 2008/0220036 A1    Sep. 11, 2008

(30) Foreign Application Priority Data
Jun. 29, 2004 (AU) ................................ 2004903510

(51) Int. Cl.
*C08K 5/053* (2006.01)
*A01N 25/08* (2006.01)
(52) U.S. Cl. ................ 523/122; 524/379; 424/409
(58) Field of Classification Search ............. 424/409; 523/122; 524/379
See application file for complete search history.

(56) References Cited

U.S. PATENT DOCUMENTS

| 5,906,825 | A * | 5/1999 | Seabrook et al. | 424/404 |
| 6,514,626 | B1 | 2/2003 | Kaas et al. | |
| 2003/0211136 | A1 * | 11/2003 | Kulkarni et al. | 424/443 |

FOREIGN PATENT DOCUMENTS

| JP | 07-228711 | 8/1995 |
| WO | WO-01/49121 | 7/2001 |

* cited by examiner

*Primary Examiner* — Kriellion A Sanders
(74) *Attorney, Agent, or Firm* — Connolly Bove Lodge & Hutz LLP (57) ABSTRACT

An antimicrobial packaging material for food stuffs containing from 0.05% to 1.5% by weight of a natural essential oil. The oil can be selected from primarily linalool and/or methylchavicol, but also from one or more of citral, geraniol, methyl cinnamate, methyl eugenol, 1,8-cineole, trans-a-bergamotene, carvacrol and thymol blended with one or more polymers selected from ethylene vinyl alcohol copolymer, polyacrylates, including ethyl acrylate methyl methacrylate copolymers, lonomers, nylons and other hydrophilic polymers or polymers possessing functional groups capable of partially anchoring the additives and the blender mix is coated onto the food contact face of a food grade packaging film or incorporated into a food grade packaging film. A binding agent such as polyethylene glycol is added to the blend to improve the retention of the volatile oil in the polymer during processing. This material has no regulatory limitations and, at the referred concentrations, does not form detectable off-flavors.

6 Claims, 5 Drawing Sheets

ANTIMICROBIAL PACKAGING MATERIAL

This application is the National Stage of International Application No. PCT/AU2005/000916 filed on Jun. 27, 2005; and this application claims priority of Application No. 2004903510 filed in Australia on Jun. 29, 2004 under 35 U.S.C. §119; the entire contents of all are hereby incorporated by reference.

This invention relates to a polymeric antimicrobial packaging material, using natural additives, particularly for use with food stuffs.

BACKGROUND TO THE INVENTION

Control of food spoiling micro-organisms, particularly on processed food stuffs, is an ever present concern in preserving food products. Various approaches such as aseptic packaging and pre-fill and post-fill sterilization are applied as a possible control method but they often result in undesirable changes in food quality characteristics. In addition fresh and many minimally processed foods cannot be preserved by such approaches and must rely on other methods. Washing in antimicrobial solutions is one possibility but protection during storage and distribution is still necessary. Incorporating antimicrobial agents in the food is another option but requires relatively large amounts of additive that increase cost and may lead to undesirable off-flavours. Modified atmosphere packaging is a common method to extend the shelf life, particularly of fresh produce, by reducing the rate of food deterioration achieved by modification of the initial concentrations of oxygen and carbon dioxide inside the package. However, these modified gas concentrations change with time. Also, some microorganisms can grow in the absence of oxygen and for some foodstuffs the absence of oxygen can affect freshness and flavour perception and even encourage the growth of harmful anaerobic microorganisms. Thus an antimicrobial agent is usually required. Synthetic antimicrobial agents in or on foodstuffs are usually not acceptable by consumers, as they prefer natural foods and food components. These additives may also accumulate above safe levels and affect flavour and taste. Antimicrobial agents are often active only against a selected range of microorganisms and those that are active against Gram-positive bacteria may not be active against Gram-negative bacteria and/or yeasts and/or moulds.

Incorporation of antimicrobial agents into packaging materials, particularly packaging films has been proposed in the past. These have generally been synthetic antimicrobial compounds. Migration of these compounds from the films into the food can be unacceptable. Generally, food safety and packaging regulations prohibit the release of (active) additives that are not approved for food content or they limit the allowable migration of such active additives from the packaging material.

USA patent application 2002/0051754 discloses an antimicrobial packaging polymer which incorporates quaternary ammonium and phosphonium salts.

There are plant extracts that possess antimicrobial activity and which are approved for use with foods. Some of them, like allyl isothiocyanate (AIT), posses a repelling smell causing unacceptable off-flavours.

Japanese abstract 03145406 discloses a rodent repellant which mixes an essential oil with an organic polymer including rubber and wood.

U.S. Pat. No. 5,688,509 discloses a controlled release insecticide for repelling insects from food, tobacco and other consumables. The active agent is incorporated in a controlled release carrier at a content above 1%.

WO00/69277 discloses an antimictobial agent for treating swine dysentery and diseases of hoofed animals using a combination of carvacrol an essential oil from oregano and thymol an essential oil from thyme.

USA application 2004/0071757 discloses an antiviral patch made by the addition of an essential oil to a pressure sensitive adhesive in concentration levels above 1%. Basil contains essential oils that exhibit activity against both Gram-positive and Gram-negative bacteria as well as against yeasts and moulds. The major active constituents of basil oil from various sources (basil varieties) are linalool, methylchavicol, citral, geraniol, methyl cinnamate, methyl eugenol, 1,8-cineole and trans-a-bergamotene. The two major components of basil, linalool and methylchavicol, possess very weak smells, not detectable at low concentrations. As the active basil oils are volatile and much of them may be lost during mixing and processing of the polymer into a packaging material, special precautions and procedures have to be followed.

It is an object of this invention to provide an antimicrobial packaging film, coating, container, or packaging component, such as labels, that uses a natural food acceptable agent in a food grade packaging material.

BRIEF DESCRIPTION OF THE INVENTION

To this end the present invention provides an antimicrobial packaging material for food stuffs which incorporates one or more volatile essential oil constituents in a relatively low temperature processable polymer composition in combination with a component that controls the release rate of the volatile oils.

By using a low temperature processable polymer composition, the loss of the volatile oil and also the risk of denaturing the oil constituents are reduced. Preferably the volatile component is mixed into a polymer component at low temperatures, or the polymer component is soaked in a solution of the volatile additive followed by evaporation of the solvent, to form a master batch which is then blended with the main polymer prior to processing and film forming. In this way higher additive retention values within the polymer are achieved. A preferred component for this process is an ethylene-vinyl acetate (EVA) copolymer which anchors and/or increases the solubility of the volatile oil components in the polymer matrix and reduces the processing temperature, resulting in a reduced evaporation of the antimicrobial additive during processing. The inclusion of a binder such as polyethylene glycol (PEG) also improves the retention rate and controls the release of the volatile oil. Other possible polymer candidates for the master batch are ethylene vinyl alcohol copolymer, polyacrylates, including ethyl acrylate methyl methacrylate copolymers, ionomers, nylons and other hydrophilic polymers or polymers possessing functional groups capable of partially anchoring the additives. A preferred film forming polymer is low density polyethylene (LDPE) blended with the EVA master batch containing the additive. These polymers are acceptable food grade packaging forming polymers.

An alternative to blending the master batch with another polymer is to coat a packaging film with the masterbatch. A preferred coating composition consists of the volatile essential oil constituent, such as a principal constituent of basil essential oil, incorporated in a polyacrylate polymer such as an ethyl acrylate methyl methacrylate copolymer. The coating may contain between 2 and 10% preferably 5% by weight of the volatile oil and between 98% and 90% preferably 95% by weight of the polyacrylate. To control the release of the volatile oil one or more additional coatings of the polyacrylate only, can coat the volatile oil layer. To minimize the volatilization of the volatile oil into the atmosphere through the polyethylene matrix (the outside of the package), a high gas barrier material may be laminated to that side of the packaging material.

The preferred concentration in the film is between 0.1% and 2.0% by weight of the total polymer structure. The concentration of the active oil required to impart antimicrobial activity for providing a sufficient shelf life is below 1.0% by weight. This concentration is low compared to prior art films. The minimum content of the additive is above 0.05% by weight. This low content saves cost in preparing the antimicrobial films. Because microbial growth and spoilage tends to occur at the surface of foodstuffs, close to the packaging film, effective control is achieved. With essential oils comprising principal constituents of herbs such as basil, thyme and oregano that are acceptable food ingredients, migration of the oils from the film is acceptable. The preferred essential oils are Linalool, methylchavicol, citral, geraniol, methyl cinnamate, methyl eugenol, 1,8-cineole, trans-a-bergamotene, carvacrol and thymol either used alone or in any combination to provide effective control against a range of microbes.

Sufficient volatile oil is added to the coating or blending masterbatch to account for loss of the active during processing to form the packaging film and during storage.

DETAILED DESCRIPTION OF THE INVENTION

Preferred embodiments of the invention are described in the following examples and the results are illustrated in the attached drawings in which.

EXAMPLE 1

The polymer films containing basil essential oils were prepared as follows:

Linalool (L260-2 from Aldrich Chemical Company) and

Methylchavicol (AUSTL 21320 from Aurora Pty Ltd) were individually blended with EVA powder into a master batch which was then mixed with LDPE to a concentration of 1.5% by weight of the polymers.

The mixture was extruded in a single screw extruder at temperatures not exceeding 160° C. and blown into a film. The films formed were transparent, and had a content of 0.34% of the active agent (linalool or methylchavicol). The performance of the films was tested with *Escherida coli* a gram negative bacteria and *Listeria innocua*.

Table 1 shows the antimicrobial activity as observed on an agar disc diffusion assay (solid media)

TABLE 1

| Treatment | Conc % w/w | Zone of inhibition mm |
| --- | --- | --- |
| LDPE | — | — no reaction |
| Linalool-LDPE | 0.34 | 11.5 ± 0.19 |
| Methylchavicol-LDPE | 0.34 | 10.1 ± 0.18 |

Figure 1:
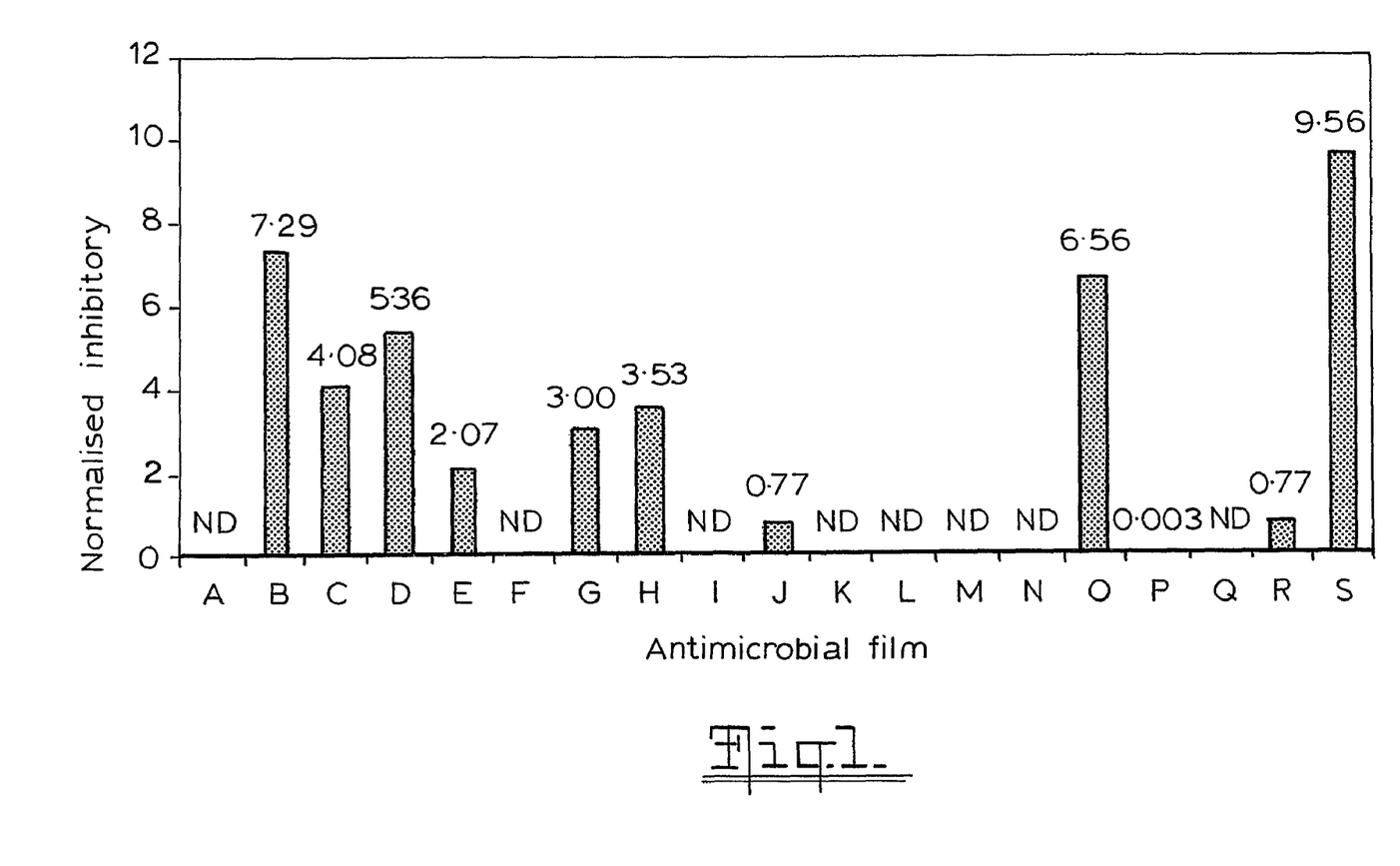
FIG. 1 illustrates the normalized inhibitory action of the antimicrobial films of this invention against *E coli* compared with films containing synthetic microbial agents.

The performance of the films of this invention compared to films containing synthetic actives is shown in FIG. 1 where B and D are the films of this invention, which achieved comparable activity compared to much greater concentrations of synthetic active agents such as O (neomycin) and S (triclosan).

The activity over time of similar films of this invention (based on linear low density polyethylene-LLDPE) is shown in Table 2

TABLE 2

| Time of valuation | Conc % w/w | Zone of inhibition mm |
| --- | --- | --- |
| After production | | |
| LLDPE | — | — no reaction |
| Linalool-LLDPE | 0.056 | 11.3 ± 1.89 |
| Methylchavicol-LLDPE | 0.053 | 8.8 ± 0.44 |
| After 1 year of storage | | |
| Linalool-LLDPE | 0.037 | 11.1 ± 0.11 |
| Methylchavicol-LLDPE | 0.028 | 8.2 ± 0.12 |

Figure 2:
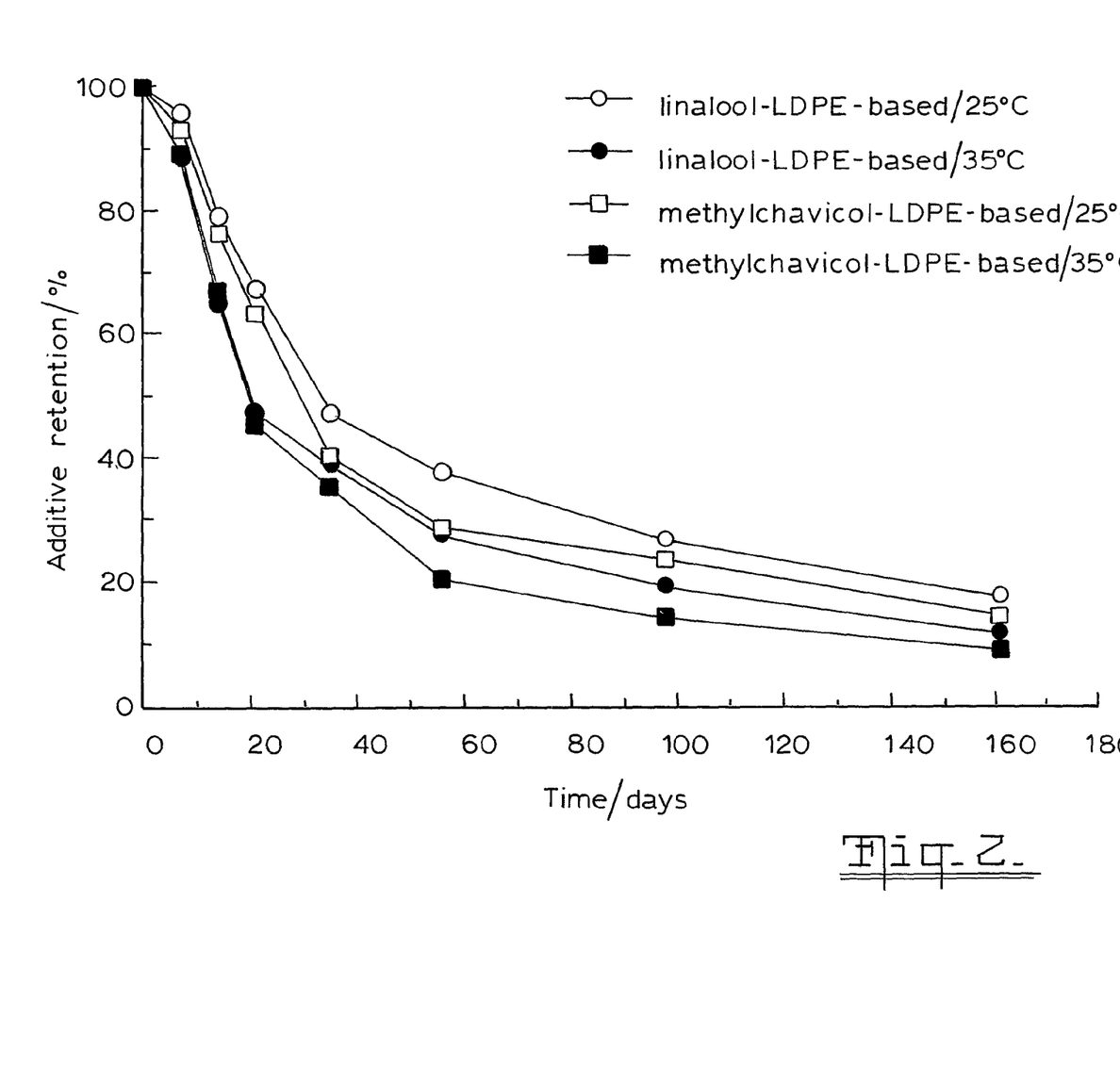
FIG. 2 illustrates the decrease in additive retention during accelerated storage of the antimicrobial film at 25 and 35° C.
Figure 3:
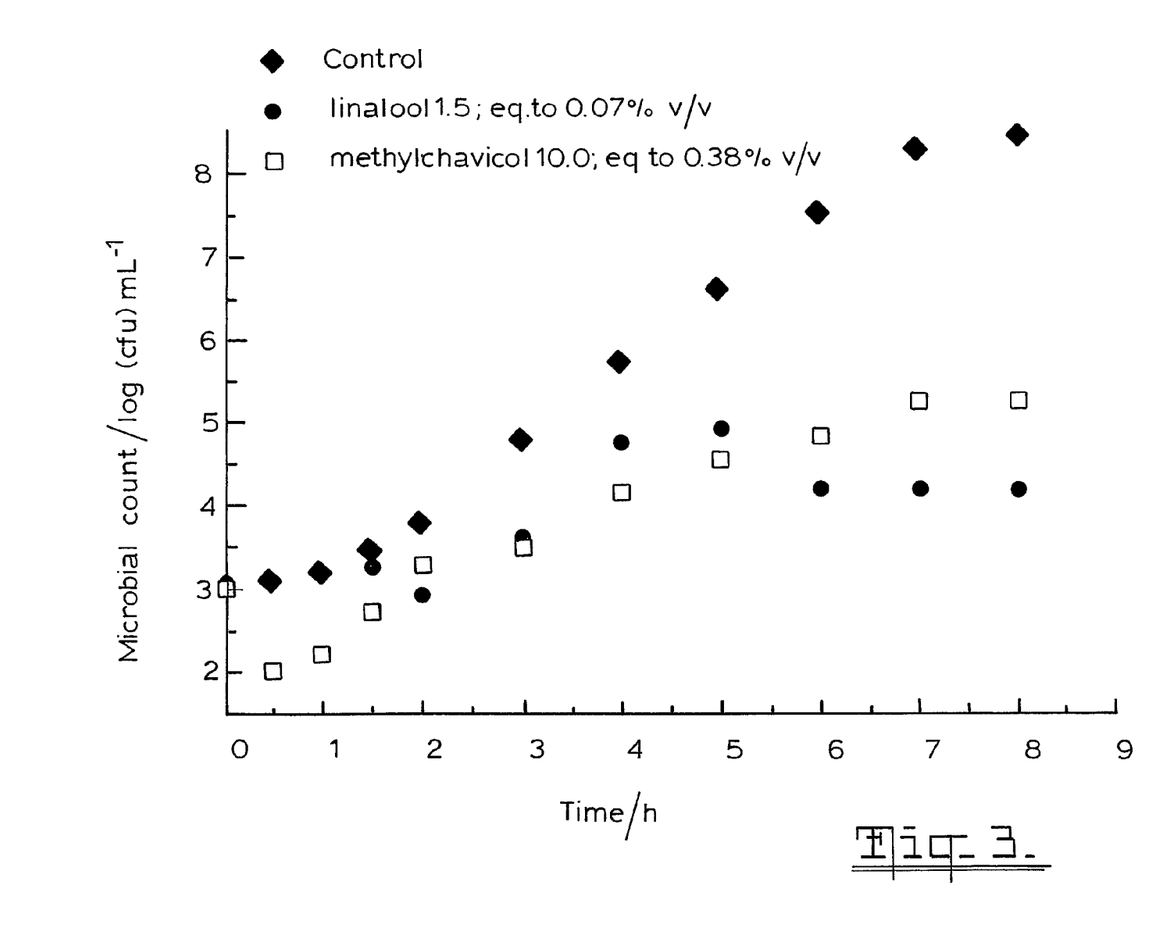
FIG. 3 illustrates the growth curve of *E coli* after addition of active agents used in the present invention.

FIGS. 2 and 3 illustrate the retention of the added compound during accelerated storage conditions and shows that sufficient additive was retained to provide protection during the projected shelf life of food products.

Figure 4:
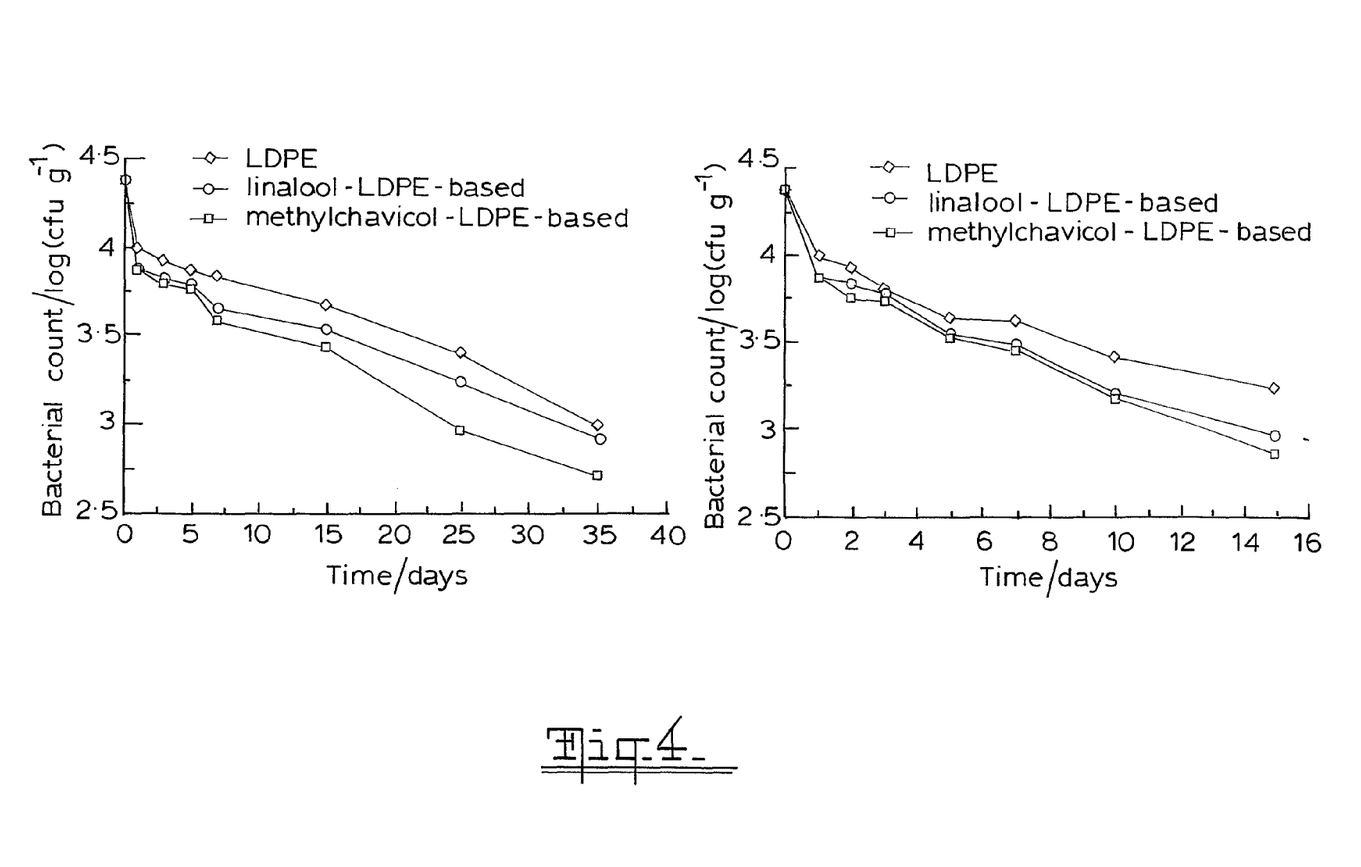
FIG. 4 graphs the inhibition of *E coli*, inoculated on the surface of Cheddar cheese.
Figure 5:
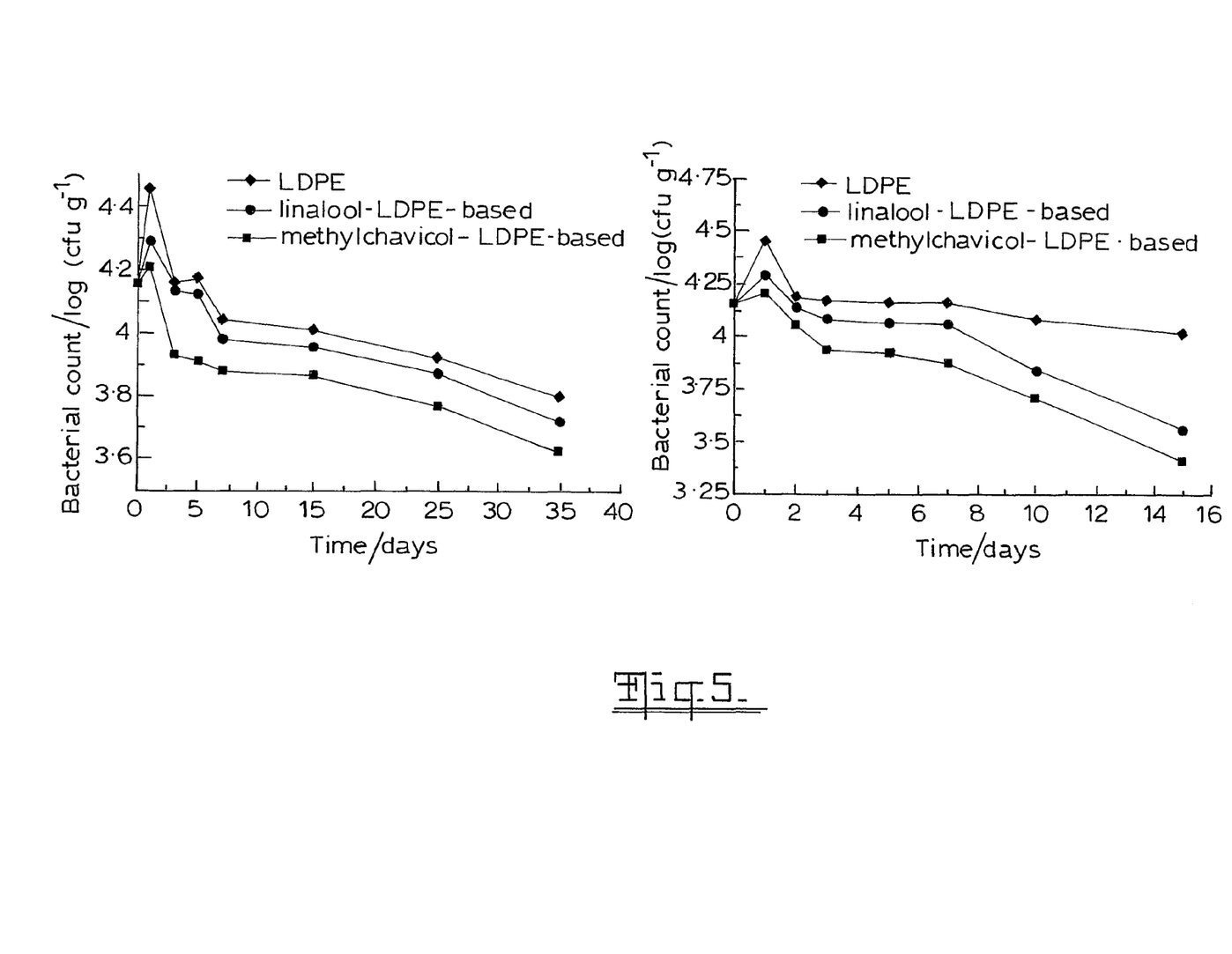
FIG. 5 graphs the inhibition of *Listeria*, inoculated on the surface of Cheddar cheese.

Commercial Cheddar cheese was sterilized under UV light and then inoculated with *Escherida coli* or *Listeria innocua* ($10^4$ cfu $g^{-1}$). The cheese was wrapped and heat sealed in plain LDPE and in films containing either linalool or methylchavicol. They were stored at 4° C. for 35 days and then a second batch was stored at 4° C. for 1 day and then at 12° C. for 15 days (temperature abuse conditions). The results of these tests are shown in FIGS. 3, 4 and 5.

EXAMPLE 2

Polymer film samples, based on various blends of LDPE, the co-polymer EVA (Ethylene Vinyl Alcohol) and the binding agent PEG (Polyethylene Glycol), containing thymol and carvacrol, either as a mixture or as a single component, were prepared from powdered LDPE (Microlene LD XJF 143/17, Qenos Pty. Ltd., Australia). Purified versions of thymol (98%) and carvacrol (98%) were obtained from Sigma-Aldrich Company Inc., Australia. The AM substances, mixed into a master batch, were incorporated into the LDPE matrix using a laboratory press.

Preparation of Films with Different Concentrations of am Agents

At the initial stage, films containing thymol or carvacrol at formulation concentrations varying from 1.0%-5.0% w/w were prepared to find the effective concentration/s of active agent retained in the sample after processing. The master batches were prepared by doping the copolymer in antimicrobial agent (in formulation concentrations of 1, 2, 3, 4, and 5% w/w respectively) dissolved in 70% v/v ethanol (EtOH).

With the aim of enhancing the retention of the antimicrobial agents, different film formulations containing 5% w/w antimicrobial agent (thymol or carvacrol), different concentrations of the binding agent and/or the copolymer were studied (Table 3). Except for the master batch preparation, the same procedure as described above was applied for the preparation of film samples of each formulation.

TABLE 3

Different formulations used for the preparation of sample films

| Formulation (F) | Composition (% w/w) | | | Master batch preparation | Preparation of final mixture | Remarks |
|---|---|---|---|---|---|---|
| | Antimicrobial agent | Binding agent | Copolymer | | | |
| F 1 | 5 | — | 10 | Doped copolymer in antimicrobial agent dissolved in 70% v/v EtOH | Mixed master batch with LDPE | No binding agent |
| F 2 | 5 | 2.5 | 5 | Doped copolymer in a mixture of antimicrobial agent and binding agent, dissolved in 70% v/v EtOH | Mixed master batch with LDPE | Copolymer % was increased at a constant level of binding agent |
| F 3 | 5 | 2.5 | 10 | | | |
| F 4 | 5 | 2.5 | — | Binding agent mixed with antimicrobial agent dissolved in 70% v/v EtOH | Mixed master batch with LDPE | No copolymer |
| F 5 | 5 | 2.5 | 10 | Doped copolymer in a mixture of antimicrobial agent dissolved in 70% v/v EtOH | Mixed master batch with LDPE containing binding agent | Binding agent incorporated at a later stage |

Films containing mixtures of thymol and carvacrol were prepared according to the Formulation 1 (F1) method as described in above. For the preparation of the film samples two AM agent mixture concentrations, 5% or 10% w/w, were applied in the formulation. Within each formulation concentration thymol and carvacrol were mixed in the ratios: 1:1, 1:2 and 2:1 respectively. Control films were prepared by incorporating the single AM compounds at a concentration of 5% w/w.

Antimicrobial Activity Assay in-vitro

The films containing a single or combinations of antimicrobial agents were assessed for antimicrobial activity against the reference microorganisms: (i) gram negative bacteria—*Esherichia coli* (UNSW 080300); *Pseudomonads aeruginosa* (UNSW 080400); (ii) gram positive bacteria—*Staphylococcus aureus* (UNSW 051300); *Listeria innocua* (ACM 4984); (iii) yeast—*Saccharomyces cerevisiae* (UNSW 703100) and (iv) fungi—*Aspergillus niger* (UNSW 80900). The test strains: *E. coli, P. aeruginosa, S. aureus, S. cerevisiae* and *A. niger* were obtained from the culture collection, University of New South Wales (UNSW), Sydney, Australia and the Australian collection of microorganisms (ACM), Dept. of Microbiology, University of Queensland, Australia.

TABLE 4

Conditions used for the growth and maintenance of test cultures

| Reference organism | Liquid medium[a] | Solid medium[b] | Incubation conditions | |
|---|---|---|---|---|
| | | | Time (h) | Temperature (C. °) |
| E. coli | NB | NA | 24 h | 37° C. |
| Listeria innocua | BHIB | BA | 24 h | 37° C. |
| Pseudomonas aeruginosa | NB | NA | 24 h | 37° C. |
| Staphylococcus aureus | NB | NA | 24 h | 37° C. |
| Aspergillus niger | MEB | MA | 1 week | 25° C. |
| Saccharomyces cerevisiae | MEB | MA | 48 h | 25° C. |

[a]NB, Nutrient Broth (Amyl, AM 131); BHIB, Brain Heart Infusion Broth (Amyl, AM 11); MEB, Malt Extract Broth (Amyl, AM 110)
[b]NA, Nutrient Agar (Amyl, AM 130); BA, Blood Agar Base C (Amyl, AM 24); MA, Malt Agar (Amyl, AM 109)

Results and Discussion

The point thickness of the sample films varied in a range of 70-140 μm. The calculated average thickness was approximately 110 μm. The average thickness was twice as high as the thickness of the extruded LDPE-based AM films used in example 1 for the determination of AM activity.

The post processing concentration of AM agent in the films is an important parameter as it directly relates to the AM activity. The post processing concentration of the AM agents, thymol and carvacrol, show a net loss during processing (Tables 5, 6 and 7) which is believed to be due to their volatile nature. The post processing retention of carvacrol was found to be better than that of thymol (Table 5). This might be attributed to the slightly higher boiling point of carvacrol (234-236° C.) than that of thymol (232° C.).

TABLE 5

| Treatment | Formulation conc. (% w/w) | Post processing conc. (% w/w) |
|---|---|---|
| Copolymer doped in Thymol before mixing with LDPE | 1.0 | 0.23 |
| | 2.0 | 0.45 |
| | 3.0 | 0.52 |
| | 4.0 | 0.74 |
| | 5.0 | 1.09 |
| Copolymer doped in Carvacrol before mixing with LDPE | 1.0 | 0.44 |
| | 2.0 | 0.65 |
| | 3.0 | 1.02 |
| | 4.0 | 1.42 |
| | 5.0 | 1.82 |

In order to enhance the retention of the AM agents, different film sample formulations using various combinations of a binding agent and a copolymer were tested (Table 3). In these formulations the concentration of AM agent was kept at a constant level (5% w/w) to ensure effective post processing concentrations. With the exception of formulation F4, the results (Table 6) show, increases in the post processing retention when the binding agent (F2, F3 and F5) is present in the films. Formulation F4, no use of the copolymer, showed the lowest retention by far. This result may indicate that the binding agent may only be capable of increasing the retention of the AM agents when the copolymer is present in the formulation. Thus, the increased retention seems to be a compound effect of the binding agent and the copolymer.

TABLE 6

Post processing retention of AM agents in LLDPE based films

| Treatment | | Post processing conc. (% w/w) | Treatment | | Post processing conc. (% w/w) |
|---|---|---|---|---|---|
| THYMOL | F1 | 0.89 | Carvacrol | F1 | 1.89 |
| | F2 | 1.36 | | F2 | 1.87 |
| | F3 | 1.90 | | F3 | 2.32 |
| | F4 | 0.50 | | F4 | 0.96 |
| | F5 | 1.60 | | F5 | 2.04 |

TABLE 7

Post processing retention of active agents in LDPE-based AM films containing mixtures of AM agents

| Treatment | Target conc % w/w | Target ratio Thymol/ Carvacrol w/w | Post processing Conc thymol | Post processing Conc carvacrol | Actual total conc | Actual ratio Thymol/ Carvacrol w/w |
|---|---|---|---|---|---|---|
| carvacrol | 5 | — | — | 1.12 | 1.12 | — |
| thymol | 5 | — | 1.73 | — | 1.73 | — |
| Mixtures 1 | 5 | 1:1 | 1.46 | 1.62 | 3.08 | 1.0:1.1 |
| | | 2:1 | 1.95 | 0.98 | 2.93 | 1.9:1.0 |
| | | 1:2 | 1.20 | 2.48 | 3.68 | 1.0:2.0 |
| Mixtures 2 | 10 | 1:1 | 2.05 | 1.83 | 3.88 | 1.1:1.0 |
| | | 2:1 | 3.96 | 2.57 | 5.79 | 1.5:1.0 |
| | | 1:2 | 2.27 | 4.22 | 6.49 | 1.0:1.8 |

The retention rates of the formulations with the mixed AM agents showed interesting results (Table 7). Although, the post processing retention of the AM agents was still less than the formulation concentration of the mixtures, the retention was substantially better when compared to the retention of the single AM agents. The retention at 5% w/w single formulation concentration as recorded in Tables 5 and 6 (F1) show losses of approximately 80% and 60% for thymol and carvacrol respectively. The 5% w/w total mixture formulations show individual losses of approximately 40% (thymol) and 35% (carvacrol).

Another interesting result was that the ratios resulted from the remaining concentrations of thymol and carvacrol in the films were quite similar to the formulation ratios.

Minimum Inhibitory Concentration (MIC)

Samples of LDPE-based films with different respective actual concentrations of thymol and carvacrol (Table 5) showed a dosage-depended AM activity in the agar disc diffusion assay (Table 8). Films containing thymol were found to be the most effective with the lowest MIC values of 0.51, 0.74 and 1.09% w/w against *Stap. aurues, S. cerevisiae* and *E. coli*, respectively.

TABLE 8

AM activity of films containing various post processing concentrations of AM agent/s as observed by agar disc diffusion assay

| | | Zone of Inhibition[2] (mm) | | |
|---|---|---|---|---|
| Treatment | Conc. (% w/w) | E. coli (3.25 × 10$^6$) | S. aurues (1.45 × 10$^7$) | S. cerevisiae (4.1 × 10$^6$) |
| Control | | —[1] | — | — |
| Thymol | 0.23 | — | — | — |
| | 0.45 | — | — | — |
| | 0.52 | — | 6.00$^b$ | — |
| | 0.74 | — | 6.12 ± 0.2$^b$ | 6.50 ± 0.7$^b$ |
| | 1.09 | 6.35 ± 0.2$^a$ | 6.90 ± 0.8$^a$ | 7.50 ± 0.7$^a$ |

TABLE 8-continued

AM activity of films containing various post processing concentrations of AM agent/s as observed by agar disc diffusion assay

| | | Zone of Inhibition[2] (mm) | | |
|---|---|---|---|---|
| Treatment | Conc. (% w/w) | E. coli (3.25 × 10$^6$) | S. aurues (1.45 × 10$^7$) | S. cerevisiae (4.1 × 10$^6$) |
| Carvacrol | 0.44 | — | — | — |
| | 0.65 | — | — | — |
| | 1.02 | — | 6.00$^z$ | 6.00$^z$ |

TABLE 8-continued

AM activity of films containing various post processing concentrations of AM agent/s as observed by agar disc diffusion assay

| | | Zone of Inhibition[2] (mm) | | |
|---|---|---|---|---|
| Treatment | Conc. (% w/w) | E. coli (3.25 × 10$^6$) | S. aurues (1.45 × 10$^7$) | S. cerevisiae (4.1 × 10$^6$) |
| | 1.42 | 6.94 ± 0.9$^y$ | 7.45 ± 0.7$^y$ | 7.33 ± 1.5$^y$ |
| | 1.82 | 8.85 ± 0.7$^x$ | 8.36 ± 0.8$^x$ | 8.25 ± 1.0$^x$ |

[1]No inhibition
[2]Means in the same column followed by same letter are not significantly (p < 0.05) different in DMR test The inhibitory effect was quite similar for these three microorganisms The effect increased significantly with the increase of AM agent concentration in the film. As expected, *Stap. aurues* (gram positive) was found to be the most sensitive followed by *S. cerevisiae* and *E. coli* respectively. However, none of the film samples showed any inhibition against *L. innocua* (gram positive) and *Ps. aeruginosa* (gram negative), although thymol and carvacrol have been reported to demonstrate AM activity against these two microorganisms (Cosentino et al., 1999; Walsh et al., 2003). The concentrations of more than 1% w/w should have been sufficient to show some AM activity.

The AM activity of the films prepared by different formulation methods varied significantly (Table 9). The addition of the binding agent to the copolymer in the master batch increased the post processing retention of AM agent in the films (Table 9). However, AM activity did not necessarily increase with the increased retention associated with the binding agent. The inhibition against *Stap. aurues, E. coli* and *S. cerevisiae* shown by the films with the binding agent is either less than or equal to that of F1 (no binding agent) films. This may be due to a reduced release of the AM agent by the binding agent.

Compared to the control, all sample films reduced significantly the colony diameter of *A. niger* (Table 9). Even films with very low concentration of active agent (e.g. F4) showed effective inhibition after 2 days and 1 week of incubation. It was found that there was no significant difference in inhibitory effect between the formulation methods. The results do not indicate an effect of a possible slower agent release by the binding agent. Thus, the addition of a binding agent may be effective in extending the activity shelf life of the AM film for long term inhibition. Several investigators support the hypothesis that the best antifungal activity of volatile compounds is achieved through gaseous contact as opposed to aqueous or agar contact (Guynot et al., 2003). The microatmospheric method as applied in the determination of AM activity of films against *A. niger* represents the activity of the active agent in its volatile state. The method may also be considered to mimic the headspace environment in a food packaging system where evaporation or equilibrated distribution of an active substance from the packaging material into the headspace and onto the food is a potential mechanism for application.

TABLE 9

Inhibition of microorganisms by AM films from different formulations

| Treatment | | Conc. (% w/w) | Zone of inhibition[2] (mm) | | | Colony diameter (mm) $A.\ niger\ (1.3 \times 10^6)$ | |
|---|---|---|---|---|---|---|---|
| | | | E. coli $(1.31 \times 10^6)$ | Stap. aurues $(1.47 \times 10^6)$ | S. cerevisiae $(3.25 \times 10^6)$ | After 2 d | After 1 wk |
| Control | | | —[1] | — | — | $41.6^{a,x}$ | $73.7^{a,x}$ |
| Thymol | F 1 | 0.89 | $7.16 \pm 1.1^a$ | $6.66 \pm 0.8^a$ | $6.63 \pm 0.6^{ab}$ | $10.3^b$ | $26.5^b$ |
| | F 2 | 1.36 | $6.24 \pm 0.5^b$ | $6.15 \pm 0.4^a$ | — | $16.6^b$ | $28.2^b$ |
| | F 3 | 1.90 | $6.05 \pm 0.5^b$ | $6.25 \pm 0.7^a$ | $6.97 \pm 1.1^a$ | $15.7^b$ | $33.2^b$ |
| | F 4 | 0.50 | — | — | — | $19.7^b$ | $39.7^b$ |
| | F 5 | 1.60 | $5.84 \pm 0.2^b$ | $6.13 \pm 0.4^a$ | $6.12 \pm 0.2^b$ | $13.6^b$ | $32.5^b$ |
| Carvacrol | F 1 | 1.89 | $7.45 \pm 1.0^x$ | $7.58 \pm 1.5^x$ | $7.35 \pm 1.3^x$ | $14.2^y$ | $33.7^y$ |
| | F 2 | 1.87 | — | $5.85 \pm 0.3^y$ | — | $18.3^y$ | $35.7^y$ |
| | F 3 | 2.32 | $6.15 \pm 0.4^y$ | $6.12 \pm 0.3^y$ | $6.50 \pm 0.7^x$ | $14.3^y$ | $40.5^y$ |
| | F 4 | 0.96 | — | — | — | $13.5^y$ | $37.7^y$ |
| | F 5 | 2.04 | $6.20 \pm 0.4^y$ | $6.18 \pm 0.4^y$ | $6.33 \pm 0.5^x$ | $13.2^y$ | $38.0^y$ |

[1]No inhibition
[2]Means in the same column followed by same letter are not significantly (p < 0.05) different in DMR test AM Activity of Mixed Agents Combination of two AM agents in the polymeric substrate had a significant effect on the AM activity (Table 10) compared with the AM activity of the single agents. Except for *S. cerevisiae*, a significantly higher inhibition was observed for film samples containing mixtures of AM agents than the films containing single compounds. It is interesting to note that films with mixture 11 (10% w/w total agent concentration in formulation) showed an inhibitory effect against *L. innocua*. The actual concentration of AM agent/s in these films may be too low for action against *L. innocua*. It was also observed that the AM efficacy may be affected by the mix ratio of the agents as is demonstrated by the results of Mixtures I ratio 1.0:2.0 compared with results of Mixtures II ratio 1.1:1.0. Although the actual total concentration is comparable in both formulations there is a significant difference in inhibitory effect for the three bacteria and *S. cerevisiae*. This indicates a possible synergistic effect that depends on the AM agent concentration ratios. However, further studies on efficacy of films with AM mixtures are needed to fully explore the synergistic or antagonistic effect on AM efficacy.

TABLE 10

Inhibition of microorganisms by LDPE-based AM films containing mixtures of AM agents

| Treatment | Total conc. (% w/w) | Ratio (thymol: carvacrol w/w) | Zone of inhibition[2] (mm) | | | | Diameter (mm) |
|---|---|---|---|---|---|---|---|
| | | | E. coli $(1.31 \times 10^6)$ | S. aurues $(1.47 \times 10^6)$ | L. innocua $(6.9 \times 10^5)$ | S. cerevisiae $(3.25 \times 10^6)$ | $A.\ niger^{[3]}$ $(1.3 \times 10^6)$ |
| Carvacrol | 1.12 | —[1] | $6.4 \pm 0.5^d$ | $6.6 \pm 0.4^c$ | — | $6.6 \pm 0.5^b$ | $32.0 \pm 1.5^b$ |
| Thymol | 1.73 | — | $6.3 \pm 0.2^d$ | $6.4 \pm 0.4^c$ | — | $6.4 \pm 0.5^b$ | $26.5 \pm 4.9^b$ |
| Mixtures I | 3.08 | 1.0:1.1 | $8.0 \pm 0.8^c$ | $8.4 \pm 2.6^b$ | — | $8.3 \pm 1.5^b$ | $5.5 \pm 0.7^c$ |
| | 2.93 | 1.9:1.0 | $7.4 \pm 0.4^c$ | $7.8 \pm 0.4^b$ | — | $9.2 \pm 1.5^b$ | $0.0^c$ |
| | 3.68 | 1.0:2.0 | $7.4 \pm 1.0^c$ | $7.8 \pm 0.4^b$ | — | $7.9 \pm 0.8^b$ | $0.0^c$ |

TABLE 10-continued

Inhibition of microorganisms by LDPE-based AM films containing mixtures of AM agents

| Treatment | Total conc. (% w/w) | Ratio (thymol: carvacrol w/w) | Zone of inhibition[2] (mm) | | | | Diameter (mm) |
|---|---|---|---|---|---|---|---|
| | | | E. coli ($1.31 \times 10^6$) | S. aurues ($1.47 \times 10^6$) | L. innocua ($6.9 \times 10^5$) | S. cerevisiae ($3.25 \times 10^6$) | A. niger[3] ($1.3 \times 10^6$) |
| Mixtures II | 3.88 | 1.1:1.0 | $11.0 \pm 0.6^{ab}$ | $10.9 \pm 0.8^a$ | $7.8 \pm 1.2^a$ | $17.5 \pm 2.5^a$ | $0.0^c$ |
| | 5.79 | 1.5:1.0 | $11.5 \pm 1.3^a$ | $10.3 \pm 0.5^a$ | $8.0 \pm 0.9^a$ | $19.4 \pm 2.5^a$ | $0.0^c$ |
| | 6.49 | 1.0:1.8 | $10.5 \pm 0.5^b$ | $11.3 \pm 1.3^a$ | $7.8 \pm 0.4^a$ | $19.9 \pm 2.9^a$ | $0.0^c$ |

[1]No inhibition
[2]Means in the same column followed by same letter are not significantly (p < 0.05) different in DMR test
[3]Colony diameter (mm) after 1 week of incubation Through variations in film component formulation and master batch preparation methods, the retention (post processing concentration) of thymol and carvacrol could be enhanced. The application of a binding agent in combination with a copolymer also increased the AM activity of the films as tested by the Agar assay method. Films containing a combination of thymol and carvacrol showed significantly increased retention as well as significantly higher AM activity. There are also indications of synergistic effects in association with agent concentration ratios.

EXAMPLE 3

Multi-coated Films Containing Natural Anti-microbial Agents Coating Solution

| | |
|---|---|
| Ethyl acrylate methyl methacrylate copolymer (40% by weight of dry substance in purified water) | 25% by weight |
| Ethanol (95% by volume) | 75% by weight |
| Linalool | from 1% by weight |

30-40% by weight of linalool is detected in the dried coating.

Films of LLDPE coated with coatings prepared as above with target concentrations of the active agent being 1% or 0.05% of the total film weight were tested for activity against E. coli and the results are shown in Table 11.

TABLE 11

AM activity of coated LLDPE films against E. coli as observed by agar disc diffusion assay

| Method | Target Conc./% w/w | Actual Conc./% w/w | Zone of Inhibition/mm |
|---|---|---|---|
| Coated without agent | — | — | —[1] |
| linalool | 1.0 | 0.9108 | $15.32 \pm 1.45^{[2]b}$ |
| | 0.05 | 0.0477 | $12.20 \pm 0.68^{[3]ab}$ |

TABLE 11-continued

AM activity of coated LLDPE films against E. coli as observed by agar disc diffusion assay

| Method | Target Conc./% w/w | Actual Conc./% w/w | Zone of Inhibition/mm |
|---|---|---|---|
| methylchavicol | 1.0 | 1.0259 | $13.52 \pm 0.57^{ab}$ |
| | 0.05 | 0.0492 | $11.31 \pm 1.00^{ab}$ |

[1]—, no reaction
[2]Values for zone of inhibition are represented as mean ± SEM
[3]The treatment with same letter within row is not statistically significant difference (p > 0.05)

From the above results it can be seen that the present invention provides a unique antimicrobial packaging material that uses a natural antimicrobial additive in an inexpensive and yet efficacious film formulation that is acceptable with foodstuffs. Those skilled in the art will appreciate that the invention may be implemented in embodiments other than those described without departing from the core teachings of the invention.

The invention claimed is:

1. An antimicrobial packaging material in which an essential oil selected from one or more of linalool, methylchavicol, citral, geraniol, methyl cinnamate, methyl eugenol, 1,8-cineole, trans-a-bergamotene, carvacrol and thymol has been blended with one or more polymers selected from ethylene vinyl acetate copolymer, polyacrylates, including ethyl acrylate methyl methacrylate copolymers, and the blended mix is compounded within a film forming polymer to form a food grade packaging film.

2. An antimicrobial packaging material as claimed in claim 1 in which the packaging material contains more than 0.05% by weight of the polymer composition of said essential oil.

3. An antimicrobial packaging material as claimed in claim 2 in which the essential oil is blended with ethylene vinyl acetate copolymer and then compounded with a low density polyethylene to form the packaging film.

4. An antimicrobial packaging material as claimed in claim 1 which incorporates a binding agent that improves the retention of a volatile oil in the polymer during processing.

5. An antimicrobial packaging material as claimed in claim 4 in which the binding agent is polyethylene glycol.

6. An antimicrobial packaging film which includes a major portion of low density polyethylene blended with a mixture of ethylenevinylacetate and linalool and/or methylchavicol so that the concentration of the linalool and/or methylchavicol is between 0.1 and 2.0% by weight of the polymer film.

* * * * *